United States Patent
Couvreur et al.

(10) Patent No.: US 8,962,552 B2
(45) Date of Patent: Feb. 24, 2015

(54) NANOPARTICLES OF THERAPEUTIC AGENTS HAVING LOW WATER SOLUBILITY

(75) Inventors: Patrick Couvreur, Villebon sur Yvette (FR); Harivardhan Reddy Lakkireddy, Malakoff (FR); Franco Dosio, Turin (IT); Barbara Stella, Turin (IT); Luigi Cattel, Pecetto (IT)

(73) Assignees: Centre Nationale de Recherche Scientifique, Paris (FR); Universite Paris SU XI, Orsay (FR)

( * ) Notice: Subject to any disclaimer, the term of this patent is extended or adjusted under 35 U.S.C. 154(b) by 728 days.

(21) Appl. No.: 12/744,424

(22) PCT Filed: Nov. 27, 2008

(86) PCT No.: PCT/FR2008/052147
§ 371 (c)(1),
(2), (4) Date: Jul. 8, 2010

(87) PCT Pub. No.: WO2009/071850
PCT Pub. Date: Jun. 11, 2009

(65) Prior Publication Data
US 2010/0305030 A1 Dec. 2, 2010

(30) Foreign Application Priority Data

Nov. 27, 2007 (FR) ...................... 07 08296

(51) Int. Cl.
*C07C 279/12* (2006.01)
*A61K 47/48* (2006.01)
(52) U.S. Cl.
CPC ..... *A61K 47/48023* (2013.01); *A61K 47/48884* (2013.01)
USPC ........................................ 514/5.9
(58) Field of Classification Search
None
See application file for complete search history.

(56) References Cited

U.S. PATENT DOCUMENTS

| 5,399,554 | A | 3/1995 | Sakamoto et al. |
| 5,489,589 | A * | 2/1996 | Wittman et al. ........... 514/232.8 |
| 7,704,972 | B2 | 4/2010 | Couvreur et al. |
| 2004/0092428 | A1 * | 5/2004 | Chen et al. ........................ 514/2 |
| 2005/0070496 | A1 | 3/2005 | Borovac et al. |
| 2005/0100577 | A1 | 5/2005 | Parker et al. |
| 2006/0198940 | A1 * | 9/2006 | McMorrow .................... 427/2.1 |

FOREIGN PATENT DOCUMENTS

| WO | WO 99/12545 | 3/1999 |
| WO | WO 00/071079 A2 | 11/2000 |
| WO | WO 2005/013968 A1 | 2/2005 |
| WO | WO 2006/090029 A1 | 8/2006 |

OTHER PUBLICATIONS

Couvreue et al., Org. Lett., 2006, 6(11), pp. 2544-2548.*
Written Opinion of the International Searching Authority issued in corresponding International Application No. PCT/FR2008/052147, mailed Oct. 9, 2009. (with English-language translation).
Couvreur et al., "Squalenoyl Nanomedicines as Potential Therapeutics," Nano Letters, 2006, vol. 6, No. 11, pp. 2544-2548.
Si et al., "Biomedical evaluation of nanomedicines," Asian Journal of Pharmacodynamics and Pharmacokinetics, 2007, vol. 7, No. 2, pp. 83-97.
Kingston et al., "Taxoids: Cancer-fighting compounds from nature," Current Opinion in Drug Discovery & Development, 2007, vol. 10, No. 2, pp. 130-144.
Pasut et al., "Polymer-drug conjugation, recent achievements and general strategies," Prog. Polym. Sci. 32, 2007, pp. 933-961.
International Search Report issued in corresponding International Application No. PCT/FR2008/052147, mailed Oct. 9, 2009. (with English-language translation).

* cited by examiner

*Primary Examiner* — Brian Gulledge
(74) *Attorney, Agent, or Firm* — Oliff PLC (57) ABSTRACT

The invention relates to a water-dispersible derivative of a therapeutic agent having a low water solubility that comprises at least one molecule of said agent covalently bonded to at least one molecule of a hydrocarbon derivative having a squalenic structure or the like. The invention further relates to corresponding nanoparticles.

24 Claims, 4 Drawing Sheets

Number of days after i.v. injection of L1210 leukemia cells

NANOPARTICLES OF THERAPEUTIC AGENTS HAVING LOW WATER SOLUBILITY

The present invention is directed toward proposing water-dispersible nanoparticle, formulations of therapeutic active agents with low water solubility, which may even be hydrophobic.

In general, an active agent is said to be of low water solubility when it has a solubility in pure water of less than 100 µg/ml at room temperature, i.e. at a temperature of about 25° C.

Thus, as described hereinbelow, many therapeutic active agents and/or therapeutic candidates prove to be of low water solubility, or even totally hydrophobic, which poses appreciable difficulties as regards their therapeutic formulation. In particular, it proves to be very difficult to formulate them in a form that is compatible with systemic administration.

Admittedly, their dissolution in aqueous medium may, for some of them, be acquired provided that they are formulated in the form of organic or inorganic salts.

However, these salts or derivatives are not, in the majority of cases, readily synthetically available, and, moreover, are not always desired. The reason for this is that their preparation may take place to the detriment of the stability of the active molecule.

As illustrations of these sparingly water-soluble therapeutic active agents, mention may be made especially of cyclosporins, taxoids, taxanes and peptide molecules, for instance insulin.

Cyclosporins are antifungal compounds generally endowed with immunosuppressant activity. These cyclosporins usually show water solubility not exceeding 25 µg/ml, i.e. a value that is approximately a hundred times lower than that required for regular absorption by the body. To obtain acceptable bioavailability of cyclosporin, conventional formulations generally use dispersion systems combining a hydrophilic phase, a hydrophobic phase and a surfactant.

For their part, taxoids or taxanes, which are known for their antineoplastic properties, are diterpenic substances. Paclitaxel, which is a natural taxoid, and its semi-synthetic derivative docetaxel, are widely used for treating tumors. Taxane derivatives generally have water solubility that is even lower than that of cyclosporins. Thus, this very low water solubility has necessitated the development of specific formulations. For example, the paclitaxel formulation, distributed under the name Taxol® by Bristol Meyers Squibb and intended for systemic administration, is a sterile, non-pyrogenic formula available as a single dose containing 30 mg of anhydrous docetaxel. Besides the active agent, each dose contains polyoxyethylene glycol triricinoleate, Cremophore EL® and ethanol. Finally, this type of formulation needs to be diluted in a sterile, apyrogenic and isotonic perfusion solution (0.9% sodium chloride, 5% glucose, etc.) before administration.

Now, the presence of Cremophore EL® and ethanol, which are necessary to overcome the lack of solubility of paclitaxel, are unfortunately of a nature to cause adverse effects. Thus, to prevent any risk of manifestation of secondary hypersensitivity, the individual to be treated generally undergoes premedication with oral dexamethasone, three days before initiating the chemotherapy.

Another alternative paclitaxel formulation uses paclitaxel combined with albumin. This specific formulation is sold under the name Abraxane®. For obvious reasons, this alternative is also unsatisfactory since it imposes the formation of this derivative, by covalent bonding of an albumin molecule to a paclitaxel molecule. What is more, it cannot be totally excluded that this coupling has an effect on the therapeutic activity of paclitaxel.

Finally, it is clear that this lack of bioavailability of poorly water-soluble active agents becomes an exacerbated handicap when the active agent is intended to be administered orally, which is another route that is particularly appreciated for the administration of therapeutic active agents.

The present invention is directed specifically toward preparing a novel mode of formulation of poorly water-soluble therapeutic active agents that can overcome the drawbacks of the conventional formulations of such active agents.

The present invention results more particularly from the observation by the inventors that it proves possible to formulate these poorly water-soluble or even hydrophobic therapeutic active agents, in the form of nanoparticles suspended in an aqueous medium and of reduced size, which is especially compatible with administration by injection, with the proviso that these active agents are combined with a squalene derivative or analog.

Thus, according to a first aspect, the present invention relates to a water-dispersible derivative of a therapeutic active agent of low water solubility formed from at least one molecule of said active agent covalently coupled with at least one molecule of a hydrocarbon-based compound of squalene structure or an analog thereof.

More specifically, the present invention relates to an abovementioned water-dispersible derivative in which the therapeutic active agent used has a solubility of less than 100 µg/ml in pure water measured at room temperature, in particular less than 25 µg/ml, especially less than 20 µg/ml or even less than 10 µg/ml and more particularly less than 5 µg/ml.

For the purposes of the present invention, such a derivative may also be referred to as a "conjugate".

More particularly, according to another of its aspects, the present invention relates to water-dispersible nanoparticles of at least one therapeutic active agent of low water solubility in which said active agent is present therein in a form combined with at least one hydrocarbon-based compound of squalene structure or an analog thereof.

In document PCT/FR2005/050 488, the inventors already mentioned the capacity of squalene, when it is covalently coupled to gemcitabine, a polar hydrophilic molecule, to spontaneously form nanoparticles of about a hundred nanometers in aqueous medium. This capacity is especially explained therein by the amphiphilic behavior of the derivatives thus synthesized, the squalene part representing the hydrophobic part and the gemcitabine part the hydrophilic part.

Now, contrary to all expectation, the inventors have found that placing derivatives of therapeutic active agents that are of low water solubility or even hydrophobic, resulting from the covalent coupling of at least one molecule of said therapeutic active agent with at least one molecule of a hydrocarbon-based compound with a squalene backbone, in the presence of a polar solvent, for instance water, also leads to the spontaneous formation of particles of a few tens to a few hundred nanometers, which are thus advantageously compatible with systemic administration and which remain endowed with the therapeutic efficacy of the active agent under consideration.

Formulating these hydrophobic therapeutic active agents in the form of nanoparticles in accordance with the present invention thus constitutes an advantageous alternative to the already-existing formulations.

Hydrocarbon-Based Derivative of Squalene Structure

For the purposes of the present invention, a "squalene structure" is intended to denote a linear hydrocarbon-based structure formed from isoprene units, more particularly 6 of them, like squalene, the formula of which is as follows:

As illustrations of these hydrocarbon-based compounds, mention may be made more particularly of squalenic acid and derivatives thereof.

As the inventors have found, this squalene structure is particularly important in the context of the present invention since it spontaneously displays, when it is placed in contact with a polar medium and more particularly water, a compacted conformation.

Unexpectedly, the inventors have found that this capacity remains when such a derivative is combined and especially covalently bonded to another chemical species that is also of hydrophobic nature. This results in the generation of a compacted architecture in the form of nanoparticles in which the two chemical species are intimately interlaced in each other.

For the purposes of the present invention, the term "analog" denotes a hydrocarbon-based compound that is capable, on the one hand, of reproducing the behavior of a squalene derivative when it is placed in contact with a polar medium, and which is capable, on the other hand, of reproducing this capacity when it is bonded to a molecule of a therapeutic active agent of low water solubility. The substituted forms of squalene derivatives and in particular squalenic acid and its derivatives, especially of substitution, are especially covered by this definition.

Such a derivative may be, for instance, 1,1',2-tris-nor-squalenic acid, squalenoylacetic acid, 1,1',2-tris-norsqualenamine, 1,1',2-trisnorequalenol, 1,1',2-tris-norsqualenethiol, squaleneacetic acid, squalenyl-ethanol, squalenylethanethiol or squalenylethylamine.

In general, at least one hydrocarbon-based molecule of squalene structure is covalently bonded to a molecule of a therapeutic active agent of low water solubility. Needless to say, the number of molecules of hydrocarbon-based derivative that can interact with a molecule of therapeutic active agent may be greater than 1. A derivative according to the invention may comprise at least two identical or different radicals of squalene structure.

This hydrocarbon-based compound generally bears a function that is capable of reacting with a function present on the molecule of the active agent under consideration so as to establish a covalent bond between the two species, for example of ester, ether, thioether, disulfide, phosphate or amide type. Advantageously, it is a carboxylic function. In this case, the hydrocarbon-based derivative of squalene structure is squalenic acid or a derivative thereof, for instance the squalenoyl N-hydroxysuccinimidyl ester.

According to one embodiment variant, the covalent bond existing between the two types of molecule may be featured by a "linker" or connecting arm. Such an arm may especially prove to be useful when the functions respectively present on the compound of squalene structure and the therapeutic active agent of low solubility have no reactional affinity for each other and are therefore not liable to form the expected covalent bond. Such an arm makes it precisely possible to introduce via each of the two ends of its backbone adequate functions, i.e. functions respectively having the expected reactional affinity, one for the function present on the derivative of squalene structure and the other for the function present on the active agent under consideration.

It may also be envisioned that this linker also bears in its backbone a labile function, which is subsequently suitable for separating the compound of squalene structure from the therapeutic active agent. It may be, for example, a peptide unit that can be recognized by an enzyme.

Units of linker type are well known to a person skilled in the art and their use clearly falls within his competence.

Representative examples of linkers that may be envisioned according to the invention especially include (poly)amino acid units, polyols, saccharides and polyethylene glycols (polyetheroxides) of low molecular weight, in particular polyols, saccharides and polyethylene glycols (polyetheroxides) of low molecular weight.

Thus, for the purposes of the present invention, a "covalent linkage" preferably features a covalent bond especially as stated hereinabove, but also covers a covalent linkage embodied by a linker as defined previously.

Therapeutic Active Agents of Low Solubility

For the purposes of the present invention, a therapeutic active agent of low water solubility is a compound that has a solubility of less than 100 µg/ml in pure water, measured at room temperature, i.e. about 25° C., especially less than 25 µg/ml, in particular less than 20 µg/ml, especially less than 15 µg/ml or even less than 10 µg/ml and more particularly less than 5 µg/ml. For the purposes of the invention, pure water is water with a pH close to neutrality (between pH 5 and pH 8) and free of any other compound, for instance organic or mineral salts.

For the purposes of the present invention, the therapeutic active agents more particularly under consideration may be chosen from substances of groups 2 and 4 of the biopharmaceutical classification.

Representative examples of these substances of low water solubility that may especially be mentioned include immunosuppressants, chemotherapeutic agents, especially antitumor agents, for instance taxoids, doxorubicin also known as adriamycin and its isomer epirubicin, antiangiogenic agents, antiviral agents, antibacterial agents, antibiotics and antiparasitic agents, substances acting on the metabolism of sugars, peptides, lipids, agents acting on the calcium channels, nonsteroidal antiflogistic agents and peptide compounds, for instance insulin.

It is understood that, in the context of the present invention, it is only the hydrophobic forms or the forms of very low solubility of the abovementioned active agents that are under consideration. The ionic forms thereof or the like, which may be soluble in aqueous medium, are of no interest in the context of the invention since it is not necessary in their respect to make up for a lack of water solubility.

Thus, in the case of the present invention, the form of the active agent coupled to at least one molecule of squalene structure is generally a neutral form, i.e. a nonionic or nonsalified form unless this form itself proves to be of low water solubility.

Immunosuppressants are hydrophobic compounds and comprise N-methylated cyclic undecapeptides. Among this family of active agents, cyclosporins are more particularly under consideration. They are especially cyclosporins A and G. However, other macrolides may also be considered according to the invention.

It may also be a case of an immunosuppressant such as deoxyspergualine, rapamycin or ascomycin.

According to one preferred variant of the invention, the therapeutic active agents of low solubility are more particularly taxanes and taxoids.

Such compounds are especially described in patent application WO 2005/013 968. It is more preferably docetaxel, paclitaxel or a derivative thereof.

As stated previously, these substances are functionalized with at least one molecule of a hydro-carbon-based compound of squalene structure or an analog thereof. Thus, the therapeutic active agents under consideration according to the present invention may comprise two derivatizations, three derivatizations, or even more, these derivatizations possibly being identical or different.

The reaction necessary for establishing at least one covalent bond between a molecule of a therapeutic active agent of low water solubility and at least one molecule of a hydrocarbon-based derivative of squalene structure or an analog thereof may be performed under standard conditions and its implementation is thus clearly within the competence of a person skilled in the art.

This reaction is generally performed in solution in the presence and in an excess of at least one compound of squalene structure relative to the poorly water-soluble active agent under consideration, for example in a proportion of two equivalents, according to the standard conditions required for interacting the two specific functions borne by each of the molecules.

As non-limiting illustrations of the water-dispersible derivatives in accordance with the present invention, mention may be made most particularly of the following taxoid derivatives:

From fraction 21-32

These are two compounds derived from the functionalization of a paclitaxel molecule with, respectively, one and two squalenic acid molecules.

Other water-dispersible derivatives in accordance with the invention are:

squalenoylinsulin having the following formula:

```
H-Gly-Ile-Val-Glu-Gln-Cys-Cys-Ala-Ser-Val-Cys-Ser-
                                            10
    Leu-Tyr-Gln-Leu-Glu-Asn-Tyr-Cys-Asn-OH
                                   20
H-Phe-Val-Asn-Gln-His-Leu-Cys-Gly-Ser-His-Leu-Val-
                                             10
    Glu-Ala-Leu-Tyr-Leu-Val-Cys-Gly-Glu-Arg-Gly-Phe-
                                                 20
    Phe-Tyr-Thr-Pro-Lys-Ala-OH
``` squalenoylepirubicin having the following formula:

and squalenoyldeoxyspergualine having the following formula:

These compounds are generally obtained in the form of an aqueous dispersion.

Thus, according to another of its aspects, the present invention relates to an aqueous dispersion of at least one derivative as defined previously.

Nanoparticles According to the Invention

As stated previously, the covalent coupling of a therapeutic active agent with at least one molecule of a hydrocarbon-based compound of squalene structure is of a nature to give the active agent thus functionalized with at least one squalenoyl radical a capacity to become organized in a compacted form in a polar solvent medium, thus leading to the formation of nanoparticles.

In general, the nanoparticles thus obtained have a mean size ranging from 30 to 650 nm, in particular from 30 to 500 nm and in particular from 50 to 250 nm, or even from 100 to 200 nm, measured by light scattering using a Coulter® N4MD nanosizer from Coulter Electronics, Hialeah, USA.

Thus, the interaction of a poorly water-soluble therapeutic active agent as considered according to the invention with a hydrocarbon-based derivative in accordance with the invention, and more particularly with squalenic acid or a derivative thereof, for instance the squalenoyl N-hydroxysuccinimidyl ester, gives said therapeutic substance physicochemical characteristics that are sufficient to impart thereon a capacity to form particles whose size proves to be compatible with parenteral administration and especially intravenous administration.

According to another of its aspects, the present invention relates to a process for preparing these nanoparticles, characterized in that it comprises:

the dissolution of a derivative according to the invention, i.e. formed first by coupling at least one molecule of a hydrocarbon-based compound of squalene structure or an analog thereof with a molecule of a therapeutic active agent of low water solubility, in at least one organic solvent, for example an alcohol such as ethanol, at a concentration sufficient to obtain, during the addition of the resulting mixture, with stirring, and generally dropwise, to an aqueous phase, the instantaneous formation of nanoparticles of said derivative as a suspension in said aqueous phase, and where appropriate, the isolation of said nanoparticles.

The reaction may generally be performed at room temperature. Irrespective of its value, the reaction temperature should not affect the activity of the active agent under consideration. The process for preparing the nanoparticles according to the invention is particularly advantageous insofar as it does not require the presence of surfactants.

As stated previously, the coupling between the hydrocarbon-based derivative of squalene structure and the molecule of active agent may be direct or via a linker.

The inventors have also found that it is possible to control the size of these particles by means of the amount of therapeutic active agent used for the nanoprecipitation. Specifically, increasing the concentration of coupling product generally leads to an increase in size, and vice versa.

According to one advantageous embodiment, the nanoparticles according to the invention are formulated in the form of an aqueous dispersion with a view to their administration generally systemically.

According to one advantageous embodiment, this aqueous dispersion contains less than 5% by weight or even less than 2% by weight of $C_2$ to $C_4$ alcohol, for instance ethanol.

According to another advantageous embodiment, this aqueous dispersion contains less than 5% by weight, or even less than 2% by weight and more particularly is free of surfactant or analog, for instance polyethylene glycols, polyglycerol and derivatives thereof, for instance esters.

According to another advantageous embodiment, this aqueous dispersion contains less than 5% by weight, or even less than 2% by weight and more particularly is free of polyoxyethylenated castor oil, for instance the product sold under the name Cremophore EL®.

According to another advantageous embodiment, this aqueous dispersion intrinsically has a viscosity that is compatible with intravenous administration.

Thus, the formulation in aqueous medium of a taxoid such as Paclitaxel® using squalenic acid in the form of water-dispersible nanoparticles advantageously makes it possible to obtain a nanoparticle suspension without any additive other than 5% dextrose needed to obtain the isotonicity of the injectable suspension. It thus proves possible: (i) to dispense with the use of the toxic Cremophore, (ii) to provide a directly injectable aqueous formulation, and (iii) to administer higher concentrations of the product (up to 4 mg/ml).

According to another of its aspects, the present invention also relates to the use of these derivatives and nanoparticles in pharmaceutical compositions.

It also relates to a pharmaceutical composition comprising, as active material, at least one derivative in accordance with the present invention, especially in the form of nanoparticles.

The derivatives in accordance with the present invention may also be administered via any conventional route. However, as stated previously, given the small size of their particles, they may be administered intravenously in the form of an aqueous suspension and are thus compatible with the capillary circulation.

Another aspect of the invention thus relates to a pharmaceutical composition comprising, as active material, at least one compound in accordance with the present invention especially in the form of nanoparticles. The derivatives in accordance with the present invention may be combined therein with at least one pharmaceutically acceptable vehicle.

As examples of pharmaceutical formulations that are compatible with the compositions according to the invention, mention may be made especially of:
  intravenous injections or perfusions;
  saline solutions or solutions of purified water;
  compositions for inhalation;
  capsules, dragees and cachets especially incorporating as vehicle water, calcium phosphate, sugars, such as lactose, dextrose or mannitol, talc, stearic acid, starch, sodium bicarbonate and/or gelatin.

When the compounds are used as a dispersion in an aqueous solution, they may be combined with excipients such as sequestrants or chelating agents, antioxidants, pH regulators and/or buffer agents.

Needless to say, the nanoparticles according to the invention may bear on the surface a multitude of reactive functions, for instance hydroxyl or amine functions. It may thus be envisioned to attach to these functions molecules of all sorts, especially via covalent bonds.

As non-limiting illustrations of molecules of this type that may be combined with the nanoparticles, mention may be made especially of molecules of marker type, compounds capable of performing a targeting function, and also any compound that is capable of imparting particular pharmacokinetic characteristics thereto. As regards this last aspect, it may thus be envisioned to attach to the surface of these nanoparticles lipophilic polyethylene glycol derivatives, for instance polyethylene glycol cholesterol or polyethylene glycol phosphatidylethanolamine, or better still polyethylene glycol squalene. A surface coating based on such a compound is, in fact, advantageous for imparting increased vascular remanence on account of a significant reduction in the uptake of the nanoparticles by the liver macrophages.

Besides the abovementioned compounds, the pharmaceutical compositions according to the invention may contain agents such as preserving agents, wetting agents, solubilizers and colorants.

For obvious reasons, the amounts of derivatives according to the invention that may be used are liable to vary significantly depending on the mode of use and the route selected for their administration.

For example, for a systemic treatment with taxoid, intended for an adult patient, it may be envisioned to administer a derivative in accordance with the present invention at a dose from about 0.1 to 150 mg/kg of body weight per day and more particularly from 1 to 40 mg/kg per day.

On the other hand, for a topical administration, it may be envisioned to formulate at least one derivative in accordance with the present invention in a proportion of from 0.1% to 40% by weight or even more relative to the total weight of the pharmaceutical formulation under consideration.

It is also possible to coadminister at least one derivative in accordance with the present invention with at least one other active material that is also capable of being beneficial with regard to the pathology under consideration.

As representative examples of these active materials that may be combined with the derivatives in accordance with the present invention, mention may be made especially of other anticancer or cytostatic molecules or macromolecules (for example platinum salts, antracyclins, mitotic spindle poisons, topoisomerase inhibitors, kinase inhibitors or metalloprotease inhibitors), antiinflammatory agents of corticoid type (for example dexamethasone) or of non-corticoid type, or molecules with immunoadjuvant activity (for example antibodies with anticancer activity). The combination with the hyperthermia used in certain chemotherapies may be envisioned. The derivatives in accordance with the present invention may also be combined with surgical therapies and/or with radiation for treating cancer.

According to another of its aspects, the present invention also relates to a therapeutic treatment method comprising the administration to a patient of an effective amount of at least one derivative and/or nanoparticles according to the invention, optionally in combination with another active material and/or therapeutic means (hyperthermia, radiation) and/or surgical therapies, as defined above.

The examples and figures given below are presented as nonlimiting illustrations of the field of the invention.

FIG. 1: Accumulation of tubulin after incubating KB cells with squalenoylpaclitaxel nanoparticles (1B) relative to untreated KB cells (1A).

EXAMPLE 1

Synthesis of Monosqualenoylpaolitaxel 450 mg of paclitaxel (0.526 mmol) in dichloromethane (DCM) are reacted with 1-ethyl-3-(3-dimethylamino-propyl) carbodiimide (EDCA, 2.5 molar equivalents relative to the paclitaxel), dimethylaminopyridine (DMAP, 0.5 molar equivalent relative to the paclitaxel) and squalenic acid (2 molar equivalents relative to the paclitaxel) dissolved beforehand in DCM at room temperature. After 1 hour, the reaction is complete and stopped using water at pH 5, and extraction is performed with aqueous sodium chloride (NaCl) solution. The aqueous phase is then washed with DCM. Purification of the mixture obtained is performed by flash chromatography on SiO$_2$ (2.5×40 cm) eluted with a DCM/ethyl acetate mixture. Fractions 62-80 are collected and the monosqualenoylpaclitaxel thus obtained is characterized by $^1$H NMR (Bruker 300 MHz), mass spectroscopy (Micromass Waters ESI) and RP-HPLC.

Chemical formula: $C_{74}H_{93}NO_{15}$; MW: 1236.53

EXAMPLE 2

Synthesis of Disqualenoylpaolitaxel 450 mg of paclitaxel (0.526 mmol) in dichloromethane (DCM) are reacted with 1-ethyl-3-(3-dimethylamino-propyl) carbodiimide (EDCA, 2.5 molar equivalents relative to the paclitaxel), dimethylaminopyridine (DMAP, 0.5 molar equivalent relative to the paclitaxel) and squalenic acid (2 molar equivalents relative to the paclitaxel) dissolved beforehand in DCM at room temperature. After 1 hour, the reaction is complete and stopped using water at pH 5, and extraction is performed with aqueous sodium chloride (NaCl) solution. The aqueous phase is then washed with DCM. Purification of the mixture obtained is performed by flash chromatography on $SiO_2$ (2.5×40 cm) eluted with a DCM/ethyl acetate mixture. Fractions 21-32 are collected and the disqualenoylpaclitaxel thus obtained is characterized by $^1$H NMR (Bruker 300 MHz), mass spectroscopy (Micromass Waters ESI) and RP-HPLC.

Chemical formula: $C_{101}H_{135}NO_{16}$; MW: 1619.15

EXAMPLE 3

Preparation of Squalenoylpaolitaxel Nanoparticles 4 mg of squalenoylpaclitaxel are dissolved in 1.5 ml of ethanol (2.5 mg/ml) and added dropwise with continuous stirring (speed of 500 rpm) to 1 ml of an aqueous solution containing 5% dextrose. The squalenoylpaclitaxel self-assembles in the form of nanoparticles with a size of between 100 and 200 nm. The ethanol is then completely evaporated off under reduced pressure using a Rotavapor® to obtain a nanoparticulate suspension of squalenoylpaclitaxel at a final concentration of 4 mg/ml.

EXAMPLE 4

Preparation of other squalenoylpaolitaxel nanoparticles

Variable amounts (stated in Table 1 below) of squalenoylpaclitaxel are dissolved in 0.25 ml of tetrahydrofuran (THF). The solutions obtained are added dropwise with continuous stirring (speed of 500 rpm) to 0.25 ml of water. The squalenoylpaclitaxel precipitates in the form of nanoparticles between 100 and 200 nm in size. The THF is then completely evaporated off under reduced pressure using a Rotavapor® to obtain nanoparticulate squalenoylpaclitaxel suspensions whose size varies as a function of the concentration (see the table below).

Table 1

TABLE 1

| Squalenoyl-paclitaxel (mmol) | Diameter (nm) | Polydispersity index |
|---|---|---|
| 0.36 | 151 ± 84 | 0.39 |
| 0.88 | 169 ± 92 | 0.30 |
| 1.76 | 177 ± 99 | 0.31 |

EXAMPLE 5

Injection of the Squalenoylpaolitaxel Nanoparticles into Mice and Comparison with Taxol The nanoparticulate squalenoylpaclitaxel suspension as prepared in Example 3 (4 mg/ml) is directly injected intravenously into mice (C57BL6) at a dose of 4×50 mg/kg (paclitaxel equivalent); the injections take place on days 0, 5, 9 and 14. The injection is easy and the animals do not show any sign of toxicity. No mortality is recorded (within a period of at least one month). The direct intravenous injection of the Taxol solution (without dilution in 0.9% NaCl) leads to the immediate death of 100% of the treated mice. When the Taxol solution is prediluted in 0.9% NaCl, the maximum dose that can be injected is 20 mg/kg.

EXAMPLE 6

Anticancer Activity of the Squalenoylpaolitaxel Nanoparticles

The characterization of this activity is performed by immunofluorescence according to the following protocol:

Day 1: KB 3.1 cells originating from a human cervical carcinoma, and HT-29 cells corresponding to a human colon cancer cell line, are deposited on 6-well plates at a density of 20 000 cells/well (final volume 2 ml RPMI plus FCS). The cells are incubated at a temperature of 37° C. and at 5% $CO_2$.

Day 2: The cells are rinsed and the squalenoylpaclitaxel nanoparticles (concentration 5 µM) as prepared according to the protocol described in Example 3 are added thereto.

Day 3: After 14-16 hours, rinsing is performed twice with PBS and the extraction solution (Triton X-100 plus 0.5% PEM-PIPES 100 mM, EGTA 2 mM, $MgCl_2$ 2 mM, pH 6.8) is then added. After 4 minutes, rinsing is performed, followed by addition of 2 ml of a 3% solution of formaldehyde in PEM. 40 minutes later, rinsing is performed and 20% FCS in PBS is added over 30 minutes. Murine anti-α-tubulin FITC monoclonal antibody (diluted to 1:200) is then added and the mixture is incubated for 1 hour. It is finally rinsed with PBS and an analysis by confocal fluorescence microscopy (Leica TCS SP2) is performed.

Figure 1A:
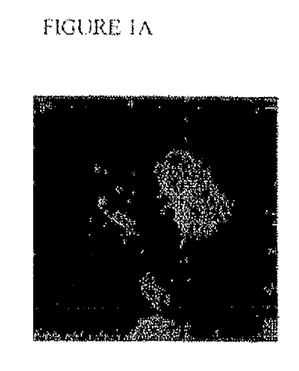
Figure 1B:
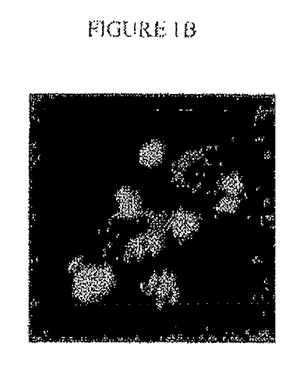

As illustrated in FIG. 1B, the formation of tubulin lumps is clearly visible by fluorescence microscopy, which shows the spindle-poisoning activity of the squalenoylpaclitaxel nanoparticles. The untreated KB cells are presented as controls (FIG. 1A).

EXAMPLE 7

Preparation of Squalenoylinsulin Nanoparticles a) Production of squalenoyl N-hydroxysuccinimidyl The reaction with insulin requires the preliminary preparation and isolation of the squalenoyl N-hydroxysuccinimidyl ester, a reactive intermediate. In practice, 300 mg (0.75 mmol) of squalenic acid dissolved in 2 ml of dichloromethane (DCM) are reacted with 72.5 mg of N-hydroxysuccinimide (2.0 molar excess) and 309 mg of dicyclohexylcarbodiimide (DCCD) (2×) dissolved in dichloromethane and stirred for 2 hours. The precipitated urea is then removed, and the mixture is dissolved in ethyl acetate, filtered and stored at a temperature of –20° C. The squalenoyl N-hydroxysuccinimidyl esters (Sq-CO—NHS) are characterized by NMR and by mass spectrometry.

b) Production of the Squalenoylinsulin Conjugate 50 mg of insulin (obtained from bovine pancreas and satisfying the criteria of the USP tests) are dissolved in 5 ml of dry dimethyl sulfoxide (>99% purity) and added to 30 µl of N,N-diisopropylethylamine in a flask containing 13.2 mg of Sq-CO—NHS (in a molar excess of 3:1). The reaction is performed at room temperature for 2 hours and the solution is dialyzed intensively in order to remove the organic solvents and the small molecular impurities, and then freeze-dried. The solid is then washed with DCM and filtered. 46 mg of white powder are obtained.

The conjugation reaction is controlled by analytical HPLC using a Waters RP C18 column (150.9 mm, 5 µm, 300 Å) and methanol/water (gradient plus 0.1% TFA) as elution solvent.

Characterization of the squalene conjugate of insulin was performed by MALDI-TOF and Orbi-Trap MS analyses.

The compound corresponds to the following structural formula:

c) Preparation of Squalenoylinsulin Nanoparticles

4 mg of the purified squalene conjugate of insulin are dissolved in dry dimethyl sulfoxide (DMSO) (1 ml) and dialyzed intensively with distilled water. The nanoparticles form during the dialysis process. The final volume is reduced to 1 ml by polyethylene glycol (PEG) 10 kDa solid concentration.

EXAMPLE 8

Preparation of Squalenoylepirubioin Nanoparticles a) Production of the 3'-amidosqualenoylepirubicin derivative 100 mg of epirubicin are rapidly dissolved in 2 ml of dry dimethylformamide (DMF) and mixed with a solution of 180 mg of squalenoyl N-hydroxysuccinimide eater (molar excess: 2.0) dissolved beforehand in dry DMF, and 20 µl of N,N-diisopropylethylamine are added. After mixing for 2 hours at a temperature of 25° C., the solution is diluted with DCM and washed with distilled water. Purification is performed by flash chromatography on SiO$_2$ (2.5×25 cm) eluted with a DCM-ethanol mixture. Fractions 60-67 are collected and 100 mg of the 3'-amidosqualenoylepirubicin conjugate are obtained and characterized by NMR and mass spectrometry. The compound corresponds to the following structural formula:

b) Preparation of Squalenoylepirubicin Nanoparticles

A volume of 200 µl of squalenoyl-3-epirubicin dissolved in acetone (10 mg/ml) is added dropwise to 5 ml of distilled water, with vigorous stirring. A fine red suspension is immediately obtained. After evaporating off the acetone under reduced pressure using a Rotavapor®, a stable nanoparticulate suspension is obtained.

EXAMPLE 9

Preparation of Squalenoyldeoxysperualine Nanoparticles a) Production of Squalenoyldeoxyspergualine Deoxyspergualine is first prepared by purifying the commercial product known as Gusperimus (Spanidine). After two chromatographic processes (ion exchange and filtration on gel), the basic form of deoxyspergualine (sparingly soluble in water) is reacted with squalenoyl N-hydroxysuccinimidyl ester. To do this, 24 mg of deoxyspergualine are rapidly dissolved in 1 ml of dry DMF, and 29 mg of squalenoyl N-hydroxysuccinimide ester (molar excess: 1.3) dissolved beforehand in the same solvent are added. 10 µl of N,N-diisopropylethylamine are then added. After mixing for 2 hours at a temperature of 25° C., the solution is diluted with DCM and washed with distilled water. Purification is performed by flash chromatography on SiO$_2$ (1.5×28 cm) eluted with DCM/ethanol plus 1% triethylamine (TEA). The fractions that were found to be positive in the Sakaguchi test (guanidine group) are then collected. 15 mg of the squalenoyldeoxyspergualine conjugate are obtained and then characterized by NMR and mass spectrometry. The squalenoyldeoxyspergualine conjugate has the following structural formula:

b) Preparation of Squalenoyldeoxyspergualine Nanoparticles

100 μl of squalenoyldeoxyspergualine dissolved in ethanol (4 mg/ml) are added dropwise to 2 ml of distilled water with vigorous stirring. After evaporating off the ethanol under reduced pressure using a Rotavapor®, a suspension of nanoparticles 162 nm in size (polydispersity index 0.12 characterized by a surface potential of 27.38±2.60 mV) is obtained.

EXAMPLE 10

Synthesis of squalenoylsuoinylpaolitaxel

Step 1

Paclitaxel is dissolved in 4-dimethylaminopyridine (0.1 eq.) and succinic anhydride (2 eq.) and dried under vacuum for 2 hours. After adding dry pyridine, the reaction mixture is stirred for 3 hours at room temperature. After removing the solvent, the crude mixture is dissolved in dichloromethane (DCM) and rinsed with brine. No additional step of purification of the paclitaxel 2'-succinate is necessary. NMR analysis to detect the absence of 2' OH, the conversion of 2' C—H (at 5.51) and the quantitative presence of 7 C—H in the normal position (4.48) shows the total conversion of the starting material into succinate derivative.

Step 2

N-Hydroxysuccinimidodiphenyl phosphate (SDPP) is prepared from diphenylphosphoryl chloride, N-hydroxysuccinimide and triethylamine (TEA) in DCM. The crude SDPP is triturated in ether, dissolved in ethyl acetate, rinsed with water, dried and concentrated under vacuum to obtain SDPP. Characterization by mass spectrometry (MS) confirms a molecular peak at 348.

To a solution of paclitaxel 2'-succinate is added SDPP (1.5 eq.) in acetonitrile with TEA (4 eq.). The reaction mixture is stirred for 6 hours at room temperature and then concentrated under vacuum. The crude reaction is dissolved in ethyl acetate and extracted with brine. The formation of paclitaxel 2'-succinyl-NHS is monitored by TLC and HPLC analyses, as described above, which avoids the need for an additional purification step.

Step 3

Squalenoyl succinyl-paclitaxel

Paclitaxel 2'-succinyl-NHS dissolved in dry dimethylformamide (DMF) is reacted with squalene amine (1 eq.) in the presence of triethylamine (1 eq.). After 8 hours at room temperature and overnight at 5° C., the mixture is extracted with brine and purified on SiO$_2$ gel, eluted with DCM-ethyl acetate. The main product (squalenoylsuccinylpaclitaxel is eluted with 30-50% ethyl acetate and its purity is controlled by HPLC analysis on an RP-18 column.

$^1$H-NMR (CDCl$_3$): d 8.13 (d, 2 h, OC(O) o-ArH), 7.75 (d, 2H, NC(O) o-ArH), 7.62 (t, 1H, OC(O) p-ArH), 7.53±7.49 (band, 3H), 7.43±7.35 (band, 7H), 6.91 (t, 1H, NH), 6.35 (s, 1H, C(10)-H), 6.27 (t, 1H, C(13)-H), 5.99 (t, 1H, C(3')—H), 5.69 (d, 1H, C(2)-H), 5.30 (dd, 1H, C(7)-H), 5.44 (dd, 1H, C(2'-H), 5.20 (s, 5H, C(sq-H), 4.97 (d, 1H, C(5)-H), 4.39±4.25 (band, 3H), 4.24±4.10 (band, 7H), 3.96 (d, 1H), 3.85 (dd, 1H), 3.75 (m, 1H), 3.42 (t, 2H, qs CH2-NH), 2.61 (p, 1H, C(6)-H and m 4H succinyl CH2), 2.46 (d, 3H, C(4)-OAc), 2.41 (m, 1H, C(14)-H), 2.29 and 2.20 (s, 4H, CH2 qs acid), 2.23 (m, 1H, C(14)-H), 2.14 (d, 3H, C(10)-OAc), 2.01 (s, 3H, C(12)-CH3), 2.00 (m, 16H, CH2 qs), 1.97 (m, 1H, C(6)-H), 1.81 (s, 3H, C(B)—CH3), 1.71 (m, 18H, C(qs)-CH3), 1.41 (d, 3H), 1.21 (s, 3H, C(15)-CH3), 1.16 (s, 3H, C(15)-CH3).

EXAMPLE 11

Synthesis of Squalenoyldiglyoolylpaolitaxel

Step 1

Squalene, in alcoholic form, is mixed with diglycolic anhydride (2.5 eq.) in dry pyridine at room temperature overnight, with stirring. The solvent is removed and the residue is extracted with dilute hydrochloric acid and brine with DCM. The conversion of the expected product is controlled by TLC. The product thus obtained is dried under vacuum and the acid is used without a further purification step.

Step 2

Squalenoyl-digucolyl-paclitaxel

Squalenediglycolic acid (2 eq.) described in step 1 is dissolved in DCM, and Paclitaxel (1 eq.) and 4-N,N-dimethylaminopyridine (3 eq.), dissolved beforehand in DCM, are then added. After 10 minutes, EDCI (1.3 eq.) is added and the solution is stirred at room temperature for 2 hours. After removing the solvent, the crude product is passed through a column of silica gel, using a DCM/ethanol gradient to obtain the purified product, the purity of which is controlled by HPLC analysis on an RP-18 column.

$^1$H-NMR (CDCl$_3$): d 8.13 (d, 2H, OC(O) o-ArH), 7.75 (d, 2H, NC(O) o-ArH), 7.62 (t, 1H, OC(O) p-ArH), 7.53±7.49 (band, 3H), 7.43±7.35 (band, 7H), 6.91 (t, 1H, NH), 6.35 (s, 1H, C(10)-H), 6.27 (t, 1H, C(13)-H), 5.99 (t, 1H, C(3')-H), 5.69 (d, 1H, C(2)-H), 5.30 (dd, 1H, C(7)-H), 5.44 (dd, 1H, C(2'-H), 5.20 (s, 5H, C(qs-H), 4.97 (d, 1H, C(5)-H), 4.39±4.25 (band, 3H), 4.33 (m, 4H diglycoyl CH2), 4.24±4.10 (band, 7H), 4.12 (m, 2H C(1) squalene), 3.96 (d, 1H), 3.85 (dd, 1H), 3.75 (m, 1H), 2.61 (p, 1H, C(6)-H), 2.46 (d, 3H, C(4)-OAc), 2.41 (m, 1H, C(14)-H), 2.29 and 2.35 (s, 4H, CH$_2$ qs acid), 2.23 (m, 1H, C(14)-H), 2.14 (d, 3H, C(10)-OAc), 2.01 (s, 3H, C(12)-CH3), 2.00 (m, 16H, CH2 qs), 1.97 (m, 1H, C(6)-H), 1.81 (s, 3H, C(8)-CH3), 1.71 (m, 18H, C(qs)-CH3), 1.41 (d, 3H), 1.21 (s, 3H, C(15)-CH3), 1.16 (s, 3H, C(15)-CH3).

EXAMPLE 12

Synthesis of squalenoylsuoinyl-PEG340-paclitaxel

Step 1

Paclitaxelsuccinyl-NHS (see Example 10, step 3) is dissolved in DCM, and a solution of tBoc-NH-PEG3-NH$_2$ (1 eq.) in DCM is added to the preceding solution with stirring. Triethylamine (0.5 eq.) is added at a temperature of 4° C., and the reaction is maintained at a temperature of 20° C. for 5 hours. The crude reaction mixture is extracted with 0.1N HCl and then with brine. The product thus obtained is used in the following step without further purification.

Step 2

Squalenoyl-succinyl-PEG 340-paclitaxel

Paclitaxelsuccinyl-PEG3-NH-tBoc is dissolved in dry DCM, and trifluoroacetic acid (TFA) is added with stirring at 20° C. After 2 hours, the reaction is complete and the mixture is extracted with a sodium acetate solution, and then with brine until neutral.

Squalene N-hydroxysuccinimide ester (1.2 eq.), prepared beforehand by reacting squalenic acid and NHS, in the presence of EDCI, is added to the paclitaxelsuccinyl-PEG3-amine (1 eq.). Triethylamine (0.3 eq.) is added and the reaction mixture is stirred at room temperature for 6 hours. After removing the solvent, the crude product is purified through a column of silica gel using a DCM/ethanol gradient in order to obtain the purified product, the purity of which is controlled by HPLC analysis on an RP-18 column.

$^1$H-NMR (CDCl$_3$): d 8.13 (d, 2H, OC(O) o-ArH), 7.75 (d, 2H, NC(O) o-ArH), 7.62 (t, 1H, OC(O) p-ArH), 7.53±7.49 (band, 3H), 7.43±7.35 (band, 7H), 6.91 (t, 1H, NH), 6.35 (s, 1H, C(10)-H), 6.27 (t, 1H, C(13)-H), 5.99 (t, 1H, C(3')—H, 5.69 (d, 1H, C(2)-H), 5.30 (dd, 1H, C(7)-H), 5.44 (dd, 1H, C(2'-H), 5.20 (s, 5H, C(qs-H), 4.97 (d, 1H, C(5)-H), 4.39±4.25 (band, 3H), 4.24±4.10 (band, 7H), 3.96 (d, 1H), 3.85 (dd, 1H), 3.75 (m, 1H), 3.42 (t, 2H, qs CH2-NH), 3.54 (m, 6H, CH2-O), 3.37 (m, 4H, O—CH2), 3.13 (m, 4H, CH2-N), 2.61 (p, 1H, C(6)-H and m 4H succinyl CH2), 2.46 (d, 3H, C(4)-OAc), 2.41 (m, 1H, C(14)-H), 2.29 and 2.20 (s, 4H, CH2 qs acid), 2.23 (m, 1H, C(14)-H), 2.14 (d, 3H, C(10)-OAc), 2.01 (s, 3H, C(12)-CH3), 2.00 (m, 16H, CH2 qs), 1.97 (m, 1H, C(6)-H), 1.81 (s, 3H, C(8)-CH3), 1.71 (m, 18H, C(qs)-CH3), 1.41 (d, 3H), 1.21 (s, 3H, C(15)-CH3), 1.16 (s, 3H, C(15)-CH3).

EXAMPLE 13

Synthesis of squalenoylC22-paolitaxel

SqualenoylC22-paclitaxel

To a solution of squalenic acid-C22 in dry DMF are added EDCA (1.5 eq.), DMAP (0.5 eq.) and paclitaxel (1.6 eq.) in DMF. After 5 hours, the reaction is quenched with water with a pH equal to 5.0 and extracted with brine.

The crude mixture is purified by chromatography on $SiO_2$, eluted with DCM/ethyl acetate using an optimized gradient. The fraction containing the expected product is eluted with 10% ethyl acetate. The pure fractions of squalenoylC22-paclitaxel are collected and the purity is controlled by HPLC analysis on an RP-18 column, of reverse-phase polarity eluted with an acetonitrile/water mixture.

$^1$H-NMR (CDCl3): d 8.13 (d, 2H, OC(O) o-ArH), 7.75 (d, 2H, NC(O) o-ArH), 7.62 (t, 1H, OC(O) p-ArH), 7.53±7.49 (band, 3H), 7.43±7.35 (band, 7H), 6.91 (t, 1H, NH), 6.35 (s, 1H, C(10)-H), 6.27 (t, 1H, C(13)-H), 5.99 (t, 1H, C(3')-H), 5.69 (d, 1H, C(2)-H), 5.30 (dd, 1H, C(7)-H), 5.44 (dd, 1H, C(2'-H), 5.20 (s, 5H, C(qs-H), 4.97 (d, 1H, C(5)-H), 4.39±4.25 (band, 3H), 4.24±4.10 (band, 7H), 3.96 (d, 1H), 3.85 (dd, 1H), 3.75 (m, 1H), 2.61 (p, 1H, C(6)-H), 2.46 (d, 3H, C(4)-OAc), 2.41 (m, 1H, C(14)-H), 2.29 and 2.35 (s, 4H, CH2 qs acid), 2.23 (m, 1H, C(14-H), 2.14 (d, 3H, C(10)-OAc), 2.01 (s, 3H, C(12)-CH3), 2.00 (m, 16H, CH2 qs), 1.97 (m, 1H, C(6)-H), 1.81 (s, 3H, C(8)-CH3), 1.71 (m, 15H, C(qs)-CH3), 1.41 (d, 3H), 1.21 (s, 3H, C(15)-CH3), 1.16 (s, 3H, C(15)-CH3).

EXAMPLE 14

Synthesis of 14-squalnoyldoxorabicin

Squalenoyl-doxorubicin

Doxorubicin in the presence of bromine and trimethyl orthoformate forms doxorubicin 14-bromo-13-dimethylacetate, which, under stirring with acetone, gives 14-bromodoxorubicin. The bromodoxorubicin dissolved in dry acetone is reacted with squalenic acid (3 eq.) in the presence of potassium carbonate. After 20 hours, the reaction is filtered, the solvent is evaporated off and the crude product is purified by chromatography on an $SiO_2$ column (4:1, DCM-methanol) to obtain 14-squalenoyldoxorubicin.

$^1$H-NMR (CDCl3): 8.02 (d, 1H, H-3), 7.87 (d, 1H, H-1), 7.70 (t, 1H, H-2), 5.46 (S, 1H, H-10), 5.3-5.25 (m, 2H, H-14a, H-14b), and 5.20 (s, 5H, C(qs-H), 5.19 (s, 1H, H-7), 4.15 (q, 1H, H-50), 4.01 (s, 3H, OCH3), 3.74 (m, 2H, H-30, H-40), 3.24 (d, 1H, H-10), 3.00 (d, 1H, H-10), 2.43 (m, 1H, H-8), 2.29 and 2.35 (s, 4H, CH2 qs acid), 2.13 (m, 1H, H-8), 2.03

(m, 16H, CH2 qs), 1.97 (m, 1H, H-20), 1.82 (m, 1H, H-20), 1.71 (m, 18H, C(qs)-CH3), 1.29 (d, 3H, CH3).

EXAMPLE 15

Preparation and Characterization of Nanoparticles of the Derivatives Synthesized According to Examples 10 to 14

Nanoparticles of various active agents are prepared by nanoprecipitation. In the case of paclitaxel, the ethanolic solution containing the squalenoyl/paclitaxel conjugate (5-10 mg/ml base solution) is added dropwise, with stirring (500 rpm), to an aqueous 5% dextrose solution. Precipitation of the nanoparticles takes place spontaneously. The organic solvents are totally evaporated off on a Rotavapor® so as to obtain an aqueous suspension of pure nanoparticles.

As regards squalenoyl-polyethylene glycol (in a ratio of 1:0.5), it is mixed in an ethanolic solution and the nanoparticles are prepared according to the method described previously.

For the preparation of squalenoyldoxorubicin nanoparticles, a mixture of dichloromethane and ethanol is used instead of pure ethanol, but the rest of the procedure is similar to that described above.

The composition of the nanoparticles formed from the conjugates previously described in Examples 10 to 14 is presented in the table below:

| Example No. | Ingredients | Amount |
| --- | --- | --- |
| 10 | Squalenoylsuccinyl-paclitaxel | 5.0 mg |
| | Squalenoyl-polyethylene glycol (MM = 2369) | 2.5 mg |
| | Dextrose | 0.05 g |
| | Water for injection | qs 1 ml |
| 11 | Squalenoyldiglycolyl-paclitaxel | 5.0 mg |
| | Dextrose | 0.05 g |
| | Water for injection | qs 1 ml |
| 12 | Squalenoylsuccinyl-PEG340-paclitaxel | 3 mg |
| | Dextrose | 0.05 g |
| | Water for injection | qs 1 ml |
| 13 | SqualenoylC22-paclitaxel | 2.5 mg |
| | Dextrose | 0.05 g |
| | Water for injection | qs 1 ml |
| 14 | Squalenoyl-doxorubicin | 2 mg |
| | Dextrose | 0.05 g |
| | Water for injection | qs 1 ml |

The mean size of the nanoparticles and the polydispersity index of the nanoparticles are determined at a temperature of 20° C. by light scattering with a zetasizer machine (Malvern Instruments, UK). The measurements are taken after diluting the nanoparticle suspension in MilliQ® water.

The size of the nanoparticles of the squalenoyl derivatives of paclitaxel and of doxorubicin and their polydispersity index are listed in the table below:

| Example No. | Type of conjugate | Mean particle diameter (nm) | Polydispersity index |
| --- | --- | --- | --- |
| 10 | Squalenoylsuccinyl-paclitaxel | 250.9 | 0.061 |
| 11 | Squalenoyldiglycolyl-paclitaxel | 150.0 | 0.075 |
| 12 | Squalenoylsuccinyl-PEG340-paclitaxel | 643.9 | 0.081 |
| 13 | squalenoylC22-paclitaxel | 239.3 | 0.077 |
| 14 | Squalenoyl-doxorubicin | 138.2 | 0.325 |

EXAMPLE 16

Evaluation of the In Vitro Anticancer Activity of the Squalenoyl Conjugates

The in vitro anticancer activity of the conjugates of squalenoyl/paclitaxel type in the form of nanoparticles is performed on Madison's 109 (M109) murine pulmonary tumor cell line. The M109 cells are cultured in RPMI 1640, supplemented with 10% fetal calf serum, 50 U·ml$^{-1}$ of penicillin and 50 µg·ml$^{-1}$ of streptomycin and 2 mM of L-glutamine. This analysis is performed using the 3-[4,5-dimethylthiazol-2-yl]-3,5-diphenyltetrazolium bromide (MTT) test, which measures the mitochondrial dehydrogenase activity. The cells in exponential growth phase are inoculated into a 96-well plate and preincubated for 24 hours at 37° C. in a humidified atmosphere with 5% $CO_2$ in the air. Various dilutions of paclitaxel nanoparticles are added to the cells in the culture medium. Each dilution is tested three times. After 72 hours at 37° C., 200 µL of MTT solution in the cell culture medium (0.5 mg/ml) are added to each well. After incubating for 2 hours 30 minutes at 37° C., the culture medium is removed and the formazan crystals obtained are dissolved in 200 µL of an extraction solution (dimethyl sulfoxide). The absorbing power of the transformed dyestuff, which is proportional to the number of viable cells, is measured at 570 nm using a microplate reader (Metertech Σ 960, Fisher Bioblock, Illkirch, France). The percentage of surviving cells is calculated by determining the ratio of the absorbing power between the treated cells and the untreated cells.

The in vitro anticancer activity of the squalenoyldoxorubicin nanoparticles is evaluated on an L1210 WT murine leukemia cell line. The cells are cultured in RPMI 1640 supplemented with 10% fetal calf serum, 50 U·ml$^{-1}$ of penicillin and 50 µg·ml$^{-1}$ of streptomycin and 2 mM of L-glutamine. The evaluation is performed according to the protocol described above.

The 50% inhibitory concentrations ($IC_{50}$) of the nanoparticles of various conjugates of squalenoyl/paclitaxel and squalenoyl-doxorubicin type are listed in the table below:

| Example No. | Type of nanoparticle | ($IC_{50}$) (µM) |
| --- | --- | --- |
| 10 | Squalenoylsuccinyl-paclitaxel | 0.072 |
| 11 | Squalenoyldiglycolyl-paclitaxel | 0.175 |
| 12 | Squalenoylsuccinyl-PEG340-paclitaxel | 0.490 |
| 13 | SqualenoylC22-paclitaxel | 7.300 |
| 14 | Squalenoyl-doxorubicin | 0.291 |

EXAMPLE 17

Evaluation of the In Vivo Anticancer Activity of Nanoparticles of a Squalenoyldiglyolyl-Paolitaxel Derivative Obtained According to Example 11

CD2F1 mice (4-5 weeks old) weighing about 15-18 g were used for this study. The mice are fed with standard mouse feed and water ad libitum. The M109 subcutaneous tumoral model (murine pulmonary tumor) is developed by injecting the M109 cells at exponential growth ($1 \times 10^6$ cells) as a suspension, under the skin, into the lower portion of the abdomen of the mice. A palpable tumor (about 50-100 mm$^3$) is allowed to grow at the site of injection. The tumor-bearing mice are divided into 2 groups of 5-6, i.e. the untreated mice and the mice treated with squalenoyldiglycolyl-paclitaxel nanoparticles 160 mg·kg$^{-1}$ (injected intravenously for 5 consecutive days). The mice are controlled regularly to check the difference in the volume of the tumors, and thus to evaluate the anticancer efficacy.

The squalenoyldiglycolyl-paclitaxel nanoparticles show anticancer activity by controlling the progression of the M109 tumors hypodermically implanted into the mice.

Figure 2:
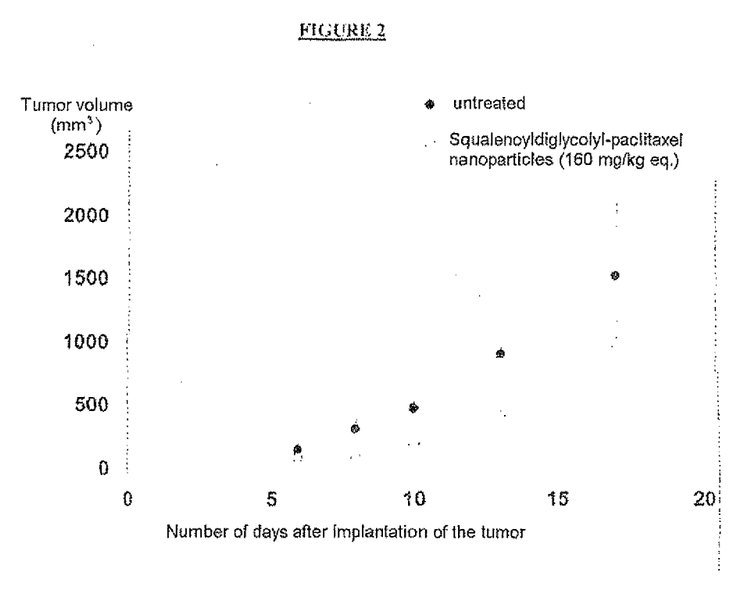
FIG. 2: Evaluation of the in vivo anticancer activity of nanoparticles of a squalenoyldiglycolyl-paclitaxel derivative obtained according to Example 11, by characterization of the volume of a tumor implanted into a mouse (in mm$^3$) as a function of time (number of days after implantation of the tumor).

These results are presented in FIG. 2.

EXAMPLE 18

Evaluation of the In Vivo Anticancer Activity of Nanoparticles of a Squalenoyldoxorubicin Derivative, Obtained According to Example 14

DBA/2 mice (4 to 5 weeks old) weighing about 15-18 g were used for this study. As for Example 17, the mice are fed with standard mouse feed and water ad libitum. The L1210 aggressive metastatic leukemia model (a murine leukemia) is developed by intravenously injecting the L1210 cells at exponential growth ($0.1 \times 10^6$ cells) as a suspension, into the mice. The tumor-bearing mice are divided into 2 groups of 5-6, i.e. the untreated mice and the mice treated with squalenoyldoxorubicin nanoparticles (13 mg·kg$^{-1}$, injected intravenously on days 1, 7 and 14, after injection of the tumor cells). After treatment, the mice are controlled regularly to check the differences in weight and the survival rate, these parameters making it possible to evaluate the efficacy of the anticancer activity.

Figure 3:
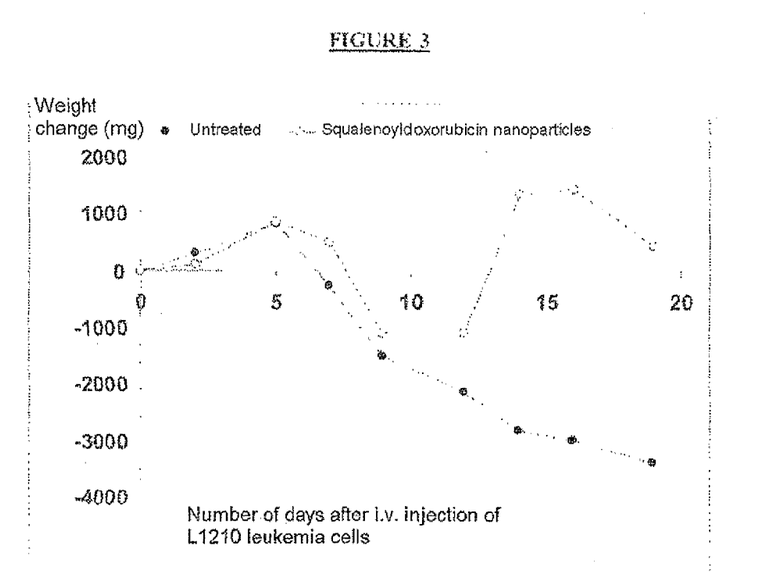
FIG. 3: Evaluation of the variations in weight of mice bearing leukemia L1210, untreated or treated with squalenoyl-doxorubicin nanoparticles, induced by metastases, as a function of time (number of days after intravenous injection of the L1210 leukemia cells).
Figure 4:
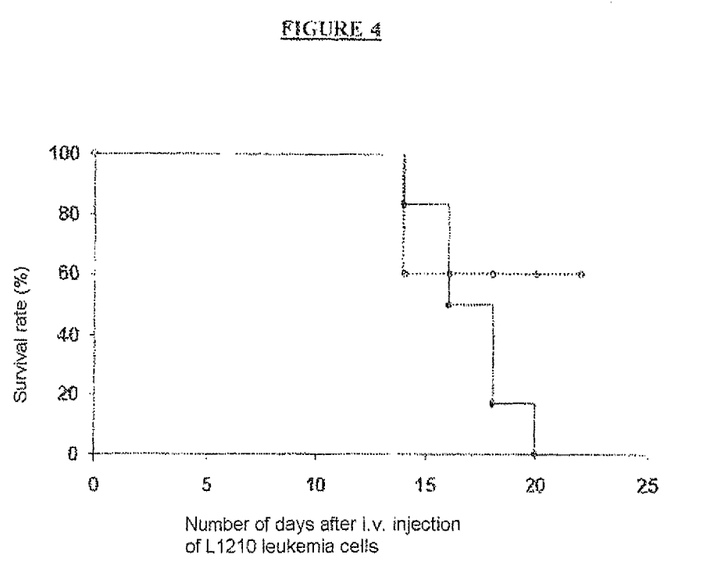
FIG. 4: Evaluation of the survival rate of mice bearing L1210 leukemia, untreated or treated with squalenoyl-doxorubicin nanoparticles, as a function of time (number of days after intravenous injection of L1210 leukemia cells).

In this model, which represents the aggressive metastatic form of cancer, the squalenoyldoxorubicin nanoparticles demonstrate effective anticancer activity (FIG. 3) and show an improved survival rate for the leukemia-bearing mice (FIG. 4).

The invention claimed is:

1. A water-dispersible derivative of a therapeutic active agent of low water solubility formed from at least one molecule of said active agent covalently coupled to at least one molecule of a hydrocarbon-based compound of squalene structure, said squalene structure being formed from 6 isoprene units, or an analog thereof, said analog being a substituted form of a squalenic acid, and said active agent having a solubility of less than 100 µg/ml in pure water, measured at room temperature, and being chosen from immunosuppressants, chemotherapeutic antitumor agents, antiangiogenic agents, antiviral agents, antibacterial agents, antibiotics and antiparasitic agents, substances acting on the metabolism of sugars or peptides, agents acting on the calcium channels, non-steroidal antiflogistic agents and peptide compounds.

2. The derivative according to claim 1, comprising at least one radical of squalene structure.

3. The derivative according to claim 1, comprising at least two identical or different radicals of squalene structure.

4. The derivative according to claim 1, said active agent of which has a solubility of less than 25 µg/ml in pure water measured at room temperature.

5. The derivative according to claim 4, wherein said active agent has a solubility of less than 20 µg/ml.

6. The derivative according to claim 5, wherein said active agent has a solubility of less than 10 µg/ml.

7. The derivative according to claim 6, wherein said active agent has a solubility of less than 5 µg/ml.

8. The derivative according to claim 1, said active agent of which is a chemotherapeutic antitumor agent chosen from taxoids, doxorubicin and epirubicin.

9. The derivative according to claim 1, said active agent of which is chosen from taxanes and taxoids.

10. The derivative according to claim 1, said active agent of which is chosen from doxetaxel, paclitaxel and a derivative thereof.

11. The derivative according to claim 1, said active agent of which is insulin.

12. The derivative according to claim 1, in which a covalent linkage existing between said therapeutic active agent of low water solubility and a molecule of said hydrocarbon-based compound of squalene structure or said analog thereof is embodied by a linker.

13. The derivative according to claim 12, in which the linker is chosen from (poly)amino acid units, polyols, saccharides and polyethylene glycols (polyetheroxides) of low molecular weight.

14. The derivative according to claim 1, chosen from:

```
H-Gly-Ile-Val-Glu-Gln-Cys-Cys-Ala-Ser-Val-Cys-Ser-
                                              10
Leu-Tyr-Gln-Leu-Glu-Asn-Tyr-Cys-Asn-OH
                    20
H-Phe-Val-Asn-Gln-His-Leu-Cys-Gly-Ser-His-Leu-Val-
                                              10
Glu-Ala-Leu-Tyr-Leu-Val-Cys-Gly-Glu-Arg-Gly-Phe-
                                              20
Phe-Tyr-Thr-Pro-Lys-Ala-OH
``` and

15. A water-dispersible nanoparticle of at least one therapeutic active agent of low water solubility in which said active agent is present therein in a form combined with at least one hydrocarbon-based compound of squalene structure, said squalene structure being formed from 6 isoprene units, or an analog thereof, said analog being a substituted form of a squalenic acid, and said active agent having a solubility of less than 100 μg/ml in pure water, measured at room temperature, and being chosen from immunosuppressants, chemotherapeutic antitumor agents, antiangiogenic agents, antiviral agents, antibacterial agents, antibiotics and antiparasitic agents, substances acting on the metabolism of sugars or peptides, agents acting on the calcium channels, non-steroidal antiflogistic agents and peptide compounds.

16. The nanoparticle according to claim 15, having a mean size ranging from 30 to 650 nm.

17. The nanoparticle according to claim 16, having a mean size ranging from 30 to 500 nm.

18. The nanoparticle according to claim 17, having a mean size ranging from 50 to 250 nm.

19. The nanoparticle according to claim 18, having a mean size ranging from 100 to 200 nm.

20. An aqueous dispersion of water-dispersible nanoparticles of at least one therapeutic active agent of low water solubility in which said active agent is present therein in a form combined with at least one hydrocarbon-based compound of squalene structure, said squalene structure being formed from 6 isoprene units, or an analog thereof, said analog being a substituted form of a squalenic acid, and said active agent being chosen from immunosuppressants, chemotherapeutic antitumor agents, antiangiogenic agents, antiviral agents, antibacterial agents, antibiotics and antiparasitic agents, substances acting on the metabolism of sugars or peptides, agents acting on the calcium channels, non-steroidal antiflogistic agents and peptide compounds.

21. A pharmaceutical composition comprising an active material in combination with at least one pharmaceutically acceptable vehicle, the active material being:
   (i) at least one water-dispersible derivative of a therapeutic active agent of low water solubility formed from at least one molecule of said active agent covalently coupled to at least one molecule of a hydrocarbon-based compound of squalene structure, said squalene structure being formed from 6 isoprene units, or an analog thereof, said analog being a substituted form of a squalenic acid, said active agent having a solubility of less than 100 μg/ml in pure water, measured at room temperature, and said active agent being chosen from immunosuppressants, chemotherapeutic antitumor agents, antiangiogenic agents, antiviral agents, antibacterial agents, antibiotics and antiparasitic agents, substances acting on the metabolism of sugars or peptides, agents acting on the calcium channels, non-steroidal antiflogistic agents and peptide compounds; or
   (ii) water-dispersible nanoparticles of at least one therapeutic active agent of low water solubility in which said active agent is present therein in a form combined with at least one hydrocarbon-based compound of squalene structure, said squalene structure being formed from 6 isoprene units, or an analog thereof, said analog being a substituted form of a squalenic acid, and said active agent being chosen from immunosuppressants, chemotherapeutic antitumor agents, antiangiogenic agents, antiviral agents, antibacterial agents, antibiotics and antiparasitic agents, substances acting on the metabolism of sugars or peptides, agents acting on the calcium channels, non-steroidal antiflogistic agents and peptide compounds.

22. A process for preparing water-dispersible nanoparticles of at least one therapeutic active agent of low water solubility in which said active agent is present therein in a form combined with at least one hydrocarbon-based compound of squalene structure, said squalene structure being formed from 6 isoprene units, or an analog thereof, said analog being a substituted form of a squalenic acid, said active agent having a solubility of less than 100 μg/ml in pure water, measured at room temperature, the process comprising at least:
- dissolving at least one water-dispersible derivative of said therapeutic active agent of low water solubility formed from at least one molecule of said active agent covalently coupled to at least one molecule of said hydrocarbon-based compound of squalene structure or said analog thereof in at least one organic solvent to obtain a mixture;
- adding the mixture, with stirring, to an aqueous phase to instantaneously form nanoparticles suspended in said aqueous phase; and
- optionally isolating said nanoparticles,
  - wherein said active agent is chosen from immunosuppressants, chemotherapeutic antitumor agents, antiangiogenic agents, antiviral agents, antibacterial agents, antibiotics and antiparasitic agents, substances acting on the metabolism of sugars or peptides, agents acting on the calcium channels, nonsteroidal antiflogistic agents and peptide compounds.

23. The process according to claim 22, in which the organic solvent is an alcohol.

24. The process according to claim 22, wherein it does not use a surfactant.

* * * * *